US00RE34728E

United States Patent [19]

Hall-Tipping

[11] E Patent Number: Re. 34,728

[45] Reissued Date of Patent: Sep. 13, 1994

[54] VIDEO GAME DIFFICULTY LEVEL ADJUSTER DEPENDENT UPON PLAYER'S AEROBIC ACTIVITY LEVEL DURING EXERCISE

[75] Inventor: Justin Hall-Tipping, Rowayton, Conn.

[73] Assignee: Heartbeat Corp., Stamford, Conn.

[21] Appl. No.: 980,685

[22] Filed: Nov. 24, 1992

Related U.S. Patent Documents

Reissue of:

[64] Patent No.: 5,001,632
Issued: Mar. 19, 1991
Appl. No.: 455,651
Filed: Dec. 22, 1989

U.S. Applications:

[63] Continuation-in-part of Ser. No. 453,448, Dec. 20, 1988, abandoned.

[51] Int. Cl.[5] ..... G06F 15/44; A61B 5/04; A63B 69/16; A63B 26/00

[52] U.S. Cl. ..... 364/413.04; 128/707; 128/905; 482/8; 364/410

[58] Field of Search ..... 364/410, 413.04; 273/148 B; 128/689, 698, 707, 905; 482/900, 4, 5, 6, 7, 8, 9

[56] References Cited

U.S. PATENT DOCUMENTS 3,159,400 12/1964 Brass et al. .
3,419,732 12/1968 Lane .
3,454,942 7/1969 Chamberlin et al. .
3,518,985 7/1970 Quinton .
3,542,012 11/1970 Frieberger et al. .
3,675,640 7/1972 Gatts .
3,834,702 9/1974 Bliss .
3,845,756 11/1974 Olsson .
3,903,613 9/1975 Bisberg .
3,991,304 11/1976 Hillsman .
4,063,551 12/1977 Sweeney .
4,112,928 9/1978 Putsch .
4,141,630 2/1979 Emmons .
4,149,716 4/1979 Scudder .
4,278,095 7/1981 Lapeyre .
4,358,118 11/1982 Plapp .
4,408,613 10/1983 Relyea .
4,512,566 4/1985 Bicocchi .
4,512,567 4/1985 Phillips .
4,530,499 7/1985 Breslow et al. .
4,542,897 9/1985 Melton et al. .
4,630,817 12/1986 Buckley .
4,637,605 1/1987 Ritchie .
4,643,421 2/1987 Meyer et al. .
4,709,917 12/1987 Yang .
4,711,447 12/1987 Mansfield .
4,720,789 1/1988 Hector et al. .
4,735,410 4/1988 Nobuta .
4,751,642 6/1988 Silva et al. .
4,790,528 12/1988 Nakao et al. .

FOREIGN PATENT DOCUMENTS 0966865 4/1975 Canada .
1183180 2/1985 Canada .

OTHER PUBLICATIONS

CALMPUTE Calmprix Road Racing Game, Thought Technology Ltd., Montreal, Quebec, 1985.
HR/BVP 100T heart rate monitor, Thought Technology, Montreal, Quebec, Jan. 1985 product catalog.
HR 100T heart rate monitor, Thought Technology, Montreal, Quebec, Mar. 1983 product catalog.
Mace, S., "Games Exhibit Innovations," InfoWorld, Jul. 9, 1984, pp. 35 and 37.

*Primary Examiner*—Donald E. McElheny, Jr.
*Attorney, Agent, or Firm*—Steve Mendelsohn; William H. Murray

[57] ABSTRACT

An exercise device, such as a exercise bicycle, is connected to a speed sensor indicating activity level, e.g. speed of the bicycle. The activity level signal, along with a heart rate signal, are provided to a video game, such as a Pac-man type video game. The game monitors the heart rate of the exerciser. If the heart rate falls outside preset minimum or maximum limits, a certain action occurs in the game, such as an increase in speed or skill level of the opposition. In the Pac-man type game for example, should the heart rate fall below the desired workout rate, the villain (the goblin) would move at a speed faster than the players' speed, putting the player at a disadvantage. The player would respond by increasing his level of physical activity, thereby increasing the heart rate until it exceeds the minimum aerobic level required, at which time the villain's speed would return to its normal level.

67 Claims, 4 Drawing Sheets

VIDEO GAME DIFFICULTY LEVEL ADJUSTER DEPENDENT UPON PLAYER'S AEROBIC ACTIVITY LEVEL DURING EXERCISE

Matter enclosed in heavy brackets [ ] appears in the original patent but forms no part of this reissue specification; matter printed in italics indicates the additions made by reissue.

This application is a continuation-in-part of application Ser. No. 07/453,448, filed Dec. 20, 1988 [;] *abandoned.*

BACKGROUND OF THE INVENTION

The present invention is directed to an exercise and video game device, and more particularly to an aerobic exercise and video game device to encourage people to commence and continue an aerobic exercise program.

It is generally accepted today that aerobic exercise promotes cardiovascular fitness. Exercise increases the continuous flow of blood through the heart and large skeletal muscles, increasing their effectiveness. More importantly, exercise helps fight, or prevent, atherosclerosis (narrowing of arteries) and coronary heart disease.

It has been estimated that 50% of all people who start an exercise program fail to keep exercising beyond three months. Though there can be many reasons for this drop out rate, a primary reason is probably the tedious nature of exercise programs.

The introduction and rapid acceptance of video games over the last ten years have, to a great extent, altered the traditional game market, certainly with regard to the younger generations. The inherently addictive nature of video games (i.e., one has to play repeatedly to gain sufficient skills to progress through all the levels of play) has probably caused those that play them to shun the traditional board games.

The present invention integrates the operations of a video game with an exercise program, in the hope that those who use this invention will find that the addictive nature of the video game will keep them involved longer in an exercise program.

Video games are usually constructed with multiple levels, each level being progressively harder to complete than the previous one. For progress to occur through all the levels of the game, the game player must learn his way through the game. This often requires repeated tries at each level, with a scoring system recording the progress achieved. Effective fitness routines share many of the characteristics of video games. Not only is fitness achieved through repeated exercise, but once the exerciser gets used to a particular level of exercise, further increases in the level of fitness are achieved only if the workout level becomes progressively harder and the workout time at the harder level is increased. This process continues until the exerciser reaches the desired standard of fitness.

For example, it would be very unlikely, and also imprudent, for an individual who is not fit to attempt a marathon on the first day of a fitness program. Similarly, it is nearly impossible for an inexperienced video player to attempt the ultimate level of expertise at his first attempt at the game. Both the exercise program and the video game player must be progressed through layered levels of increasing difficulty, each one taking perhaps a longer period of time, so that each level is perfected before the next level is attempted.

Combining exercising programs and video game playing, with the heart rate of the game player controlling the speed of the video game, would not only make exercising less tedious, but would ensure that the exerciser does not over exert himself.

Various patents have attempted to integrate video games with exercise equipment; the primary focus of these patents being to ensure that the routine of exercise is made less onerous.

U.S. Pat. No. 4,720,789 to Hector discloses a video game, or an exercise system utilizing a video display, which is played by movement of the game player's feet. The apparent objective is to require the game player to exercise while playing the game by moving his feet. However the game player is required to move at the game's speed. The game in no way alters to conform to the individual's fitness level.

U.S. Pat. No. 4,711,447 to Mansfield integrates an exercise machine with a video game. To play the game, the operator is required to move a resistance creating assembly, and in doing so, exercises. As with the previous patent, no attempt is made to adjust the video game to the player's fitness level.

U.S. Pat. No. 4,278,095 to Lapeyre discloses an exercise device connected to a video machine. The speed of the exercise device, and the accompanying video display, is controlled by the exerciser. As the exerciser signals an increase in speed to the exercise device, an accompanying signal is sent to the video machine, so that the exerciser is presented with a visual display of the increase in speed. The exerciser's heart rate is monitored and displayed on a T.V. monitor.

U.S. Pat. No. 4,512,567 to Phillips is directed to an exercise bicycle used to operate a video game. The game player receives exercise while operating the bicycle, and at the same time, moving the handlebars. The video game operates at a preset speed, thus making no allowance for the fitness of the player.

U.S. Pat. No. 4,630,817 to Buckley is directed to an exercise machine which allows for movement of a control rod, e.g. a handlebar, to provide two degrees of freedom to a controllable character in a video display. Resistance is provided to the handlebar to ensure that physical exertion is required by the user.

U.S. Pat. No. 4,709,917 to Yang discloses an exercise device which is furnished with an electronic display or a mechanical belt for simulating road conditions. A microprocessor controls the position of the exercise bicycle with respect to the scene being displayed and the running speed of the road condition simulation.

The intent of all these patents is to integrate exercise with video display. However, except for the Lapeyre U.S. Pat. No. 4,278,095 which displays the heart rate, none of them suggest monitoring the heart rate of the exerciser. Furthermore, none of them appear to disclose any means for altering the speed or skill level of the opposition in a video display in response to the output level of the exercise device falling outside a preset range.

SUMMARY OF THE INVENTION

In accordance with the present invention, a combination exercise device and game apparatus is provided. The apparatus according to the invention comprises an exercise device for aerobic activity and means for sensing the aerobic activity level of a user of said exercise device and for outputting an activity level signal having a characteristic indicative of said activity level. The apparatus further comprises a video game having at least one user operated control for controlling the actions of at least one player, regulating means for regulating the relative actions of said one player and one of an opposition piece or obstacle, display means for displaying the one player and the one of said opposition piece or obstacle, and wherein said regulating means renders the video game more difficult for the one player relative to the opposition piece or obstacle in response to activity level, as indicated by the activity level signal characteristic, falling below a first predetermined level.

The exercise device can be an exercise bicycle, treadmill or stair climbing device, for example. The means for sensing the aerobic activity level can be means for sensing the heart rate of the user of the exercise device, or can be means for sensing the output of the exercise device. The regulating means may further increase the speed of the opposition piece or obstacle relative to the one player in response to the heart rate of the user falling below the first predetermined level. The first predetermined level may correspond to the minimum aerobic activity level for the user, which can be selected according to the user's age. The regulating means may preferably render the video game less difficult to the one player in response to the activity level exceeding a second predetermined level, where the second predetermined level is greater than said first predetermined level. The second predetermined level preferably corresponds to the maximum heart rate of the user in an optimum aerobic exercise range.

If the regulating means is responsive to the user's heart rate and the means for sensing also senses the output of the exercise device, the apparatus may be arranged so that the speed of the player and the opposition piece or obstacle both increase or decrease, respectively, in response to the increase or decrease, respectively, of the output of the exercise device. The display means may display the heart rate of the user, and/or the output level of the exercise device.

According to another aspect of the invention, a game apparatus useable with an exercise device is provided comprising means for sensing the aerobic activity level of a user of an exercise device and for outputting an activity level signal having a characteristic indicative of said activity level, and a video game having at least one user operated control for controlling the actions of at least one player, display means for displaying the one player and the one of said opposition piece or obstacle, and wherein said regulating means renders the video game more difficult for the one player relative to the opposition piece or obstacle in response to activity level, as indicated by the activity level signal characteristic, falling below a first predetermined level.

According to another aspect of the invention, an exercise motivation apparatus is provided which is useable with an exercise device and a video game having at least one user operated control for controlling the actions of at least one player, and which controls the relative actions said one player and of one of an opposition piece or obstacle, and which displays the one player and the one of said opposition piece or obstacle, comprising means for sensing the aerobic activity level of a user of an exercise device, and for outputting an activity level signal having a characteristic indicative of said activity level and regulating means for rendering the video game more difficult for the one player relative to the opposition piece or obstacle in response to activity level, as indicated by the activity level signal characteristic falling below a first predetermined level.

In accordance with one form of the present invention, a controller, with three inputs, is integrated with a video game. The first input is from a speed sensor connected to an exercise machine. The speed sensor measures the speed with which an exercise machine is being used. The second input is from a heart rate monitor that is attached to the person using the exercise machine. The third input is from a joystick that is operated by the exerciser.

In the standard format of a video game, a game player, using some form of joystick, maneuvers a player or playing piece in the form of an object (the source) through the game, encountering one or more opposition pieces and/or various obstacles sometimes called villains to his progress along the way. The obstacles are usually designed to destroy the game player's piece. The source and villains' speed are preset in the game's computer source code. Each game continues until all the game players' lives have been used up. A point counting system measures the game player's progress through the game. As used herein the term player refers to the playing piece controlled by the exerciser, and can be an object or even a weapon as shown on the video display. The term opposition or obstacle means any playing piece which serves as an obstacle, opposition or adversary to the player and can be a target if the player is a weapon. Of course, the player can be a target, in which case the opposition may be or may have a weapon.

In this invention, the mechanics of the video game are altered to integrate an individual's exercise routine. The speed the source moves in the video game is determined by the speed that the exerciser is using the exercise equipment. This is measured by the speed sensor. Directional movement of the source may be controlled using a standard joystick. The speed of the villain is determined according to the game player's pulse, recorded with the heart rate monitor.

An exerciser, prior to commencing a workout, inputs his age, and the preferred duration of his warm-up and workout. According to a preset formula, the controller sets upper and lower heart rates for the duration of the exercise routine. These heart rates may be overridden by user input. Once the exerciser commences the exercise routine, the controller continually checks the pulse of the exerciser against the upper and lower optimal exercise heart rates for that individual. If the heart rate falls outside the preset limits or bands at any time throughout the exercise routine the speed of the game is altered. Where the video game is the PAC-MAN video game for example, if the heart rate of the exercising individual falls below the preset minimum optimal heart rate, the villain, in this game the Goblin, would move faster than its normal speed. This should prompt the game player to speed up on the exercise machine, thereby increasing the speed of the source, called the PAC-MAN player Pac-man, to escape the Goblin.

The primary object of the invention is to keep people motivated to exercise, and particularly to exercise within an optimal range of heartbeats per minute. Since the exerciser will become fitter over time, the speed of the exercise machine needed to keep the heart rate within the optimal aerobic range would increase. The video game continually motivates the game player to maintain aerobic efficiency.

The video game may include a display such as a bar graph, indicating the present heart rate, and its relation to the minimum and maximum limits.

Further objects and advantages will become apparent in conjunction with the following detailed description, claims and accompanying drawings.

DESCRIPTION OF THE PREFERRED EMBODIMENT

Figure 1:
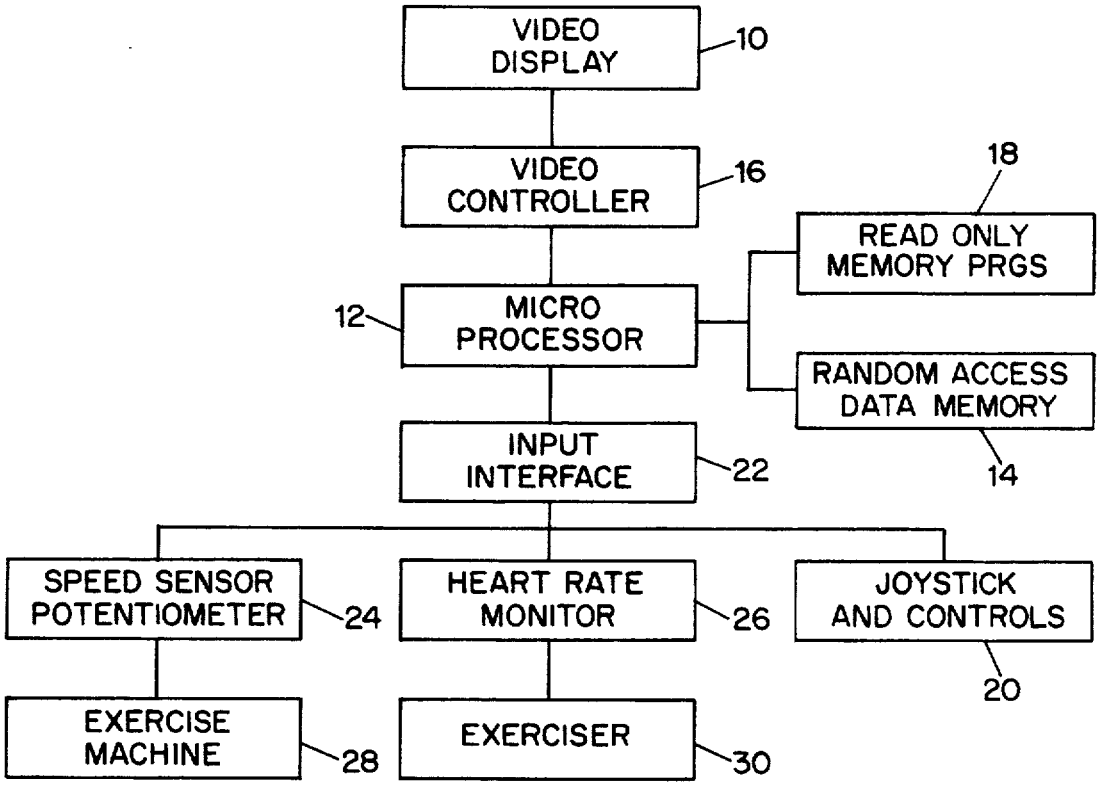
FIG. 1 is a block diagram of an exercise and video game device according to the invention with controller and input devices.

FIG. 1 is a block diagram of a video game includes a video display 10, a microprocessor 12, random access data memory 14, a video controller 16, read only memory 18 for storing programs and a hand operated joystick and other controls or inputs 20. The hand operated joystick 20 may also be in the form of an x-direction control which is mounted on the exercise machine 28 for operation by one of the user's hands, and a y-direction control mounted for the other user's hands. Also shown are a speed sensor 24, connected to an exercise machine 28, (for example an exercise bicycle, treadmill or stair climbing exerciser), and a heart rate monitor 26, which is used to measure the pulse of the exerciser 30, i.e. the user of the exercise machine. The speed of the exercise bicycle and the pulse rate are passed via the input interface 22 to the game microprocessor 12.

Before discussing the operation of the preferred embodiment and program operation according to the flowchart in FIG. 4, a discussion of a typical fitness program will be given first.

Figure 2:
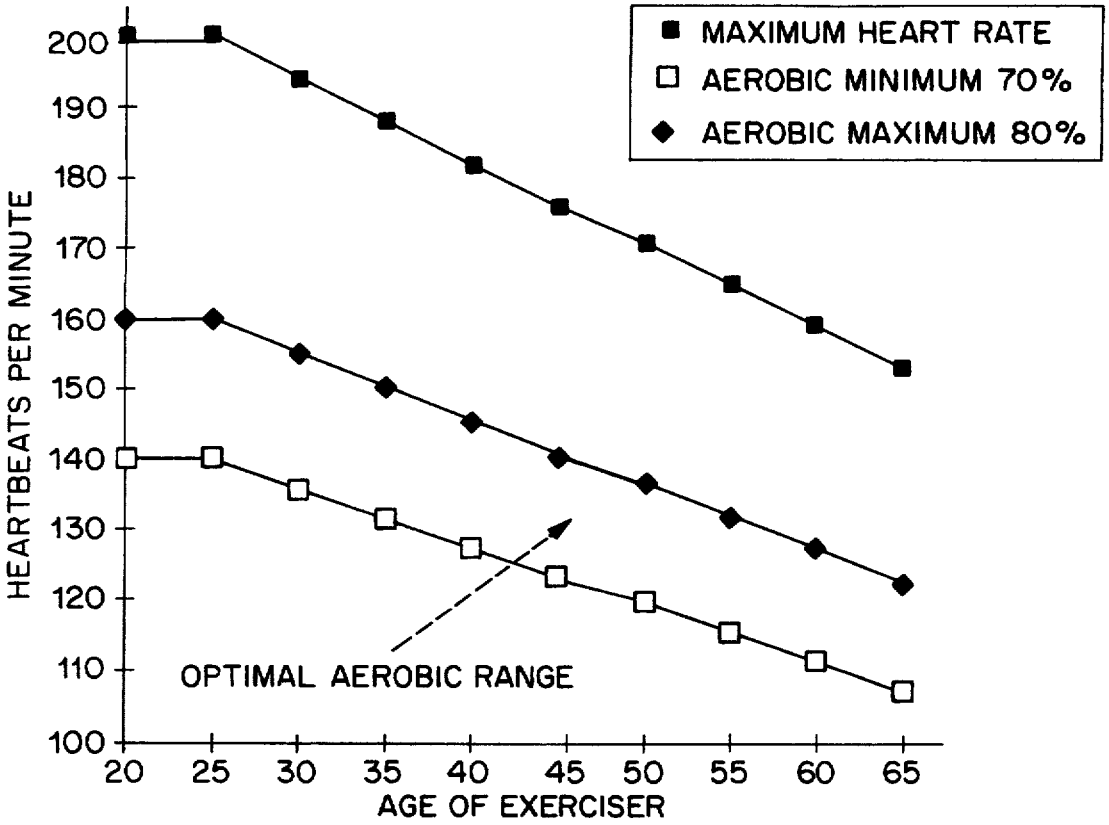
FIG. 2 (PRIOR ART)
FIG. 2 illustrates the optimal heart rate during aerobic exercise.
Figure 3:
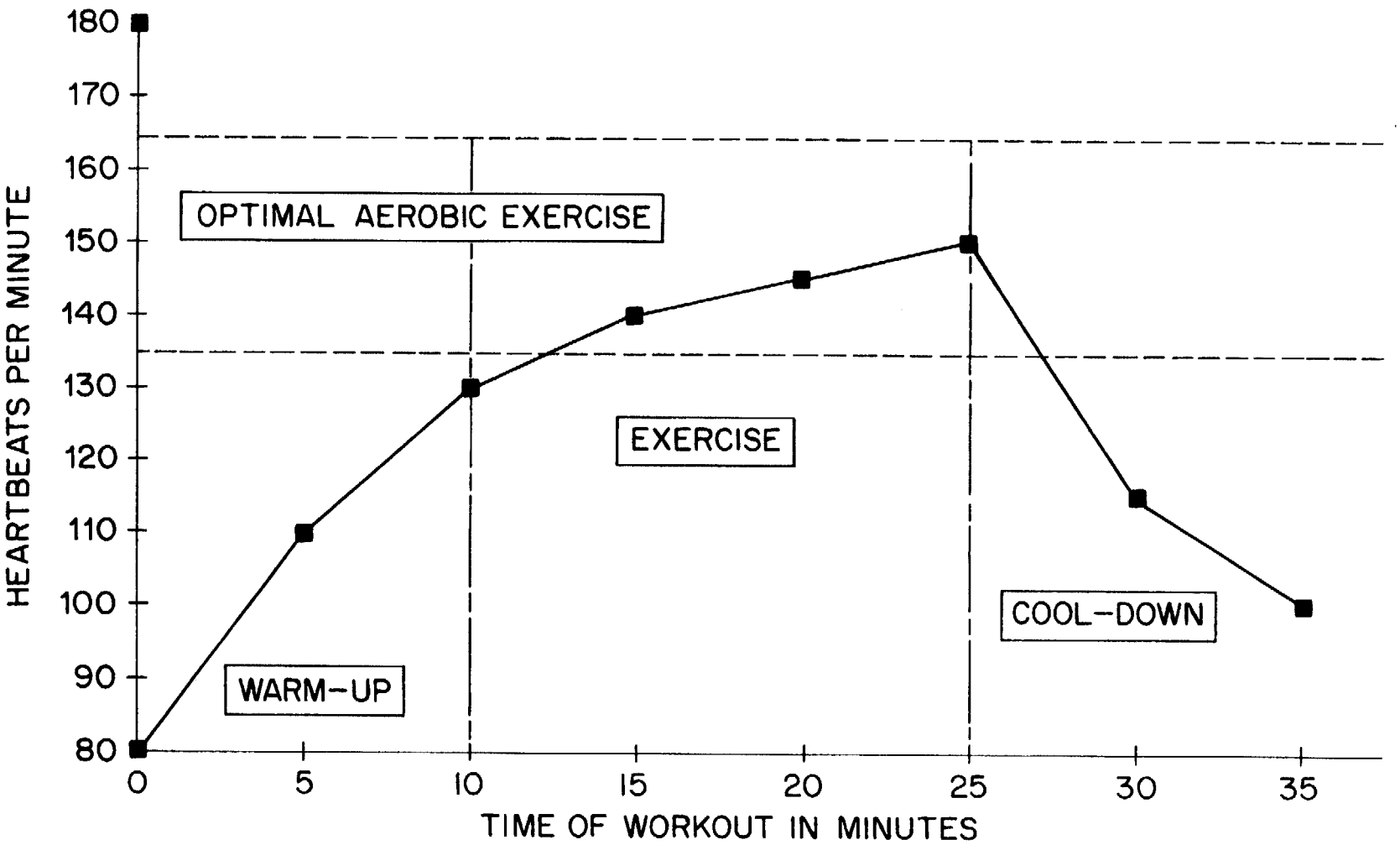
FIG. 3 (PRIOR ART)
FIG. 3 is an example of an optimal exercise routine for a 30 year old individual.

Physicians recommend that aerobic exercise should be maintained for a period of twenty minutes at least three times per week. The optimal level of activity is for exercise to increase the pulse rate to between 70% and 80–85% of maximum attainable heart rate (approximately found using the formula of 220 minus the user's age in years). (FIG. 2) Fitness authorities recommend that fitness programs consist of three parts: warm-up, work-out and cool-down. (See FIG. 3):

(a) Warm-up period—between 5 and 10 minutes. The heart beat should not exceed 50% of the user's maximal heart rate at the conclusion of the warm-up period.

(b) Work-out—Period of vigorous exercise within the recommended aerobic range as determined by the user's heart or pulse rate.

(c) Cool-down—easing up on the exercise intensity over a 5 to 10 minute period before stopping. The pulse at the end of the cool down period should be back to less than 50 percent of maximal attainable heart rate.

It is important that while alleviating the boredom of exercise with interactive video games, one does not encourage the exerciser to over-exert his heart. In accordance with the present invention, means are provided, as will be described, to encourage an exerciser to stay above the minimum recommended aerobic level, but at the same time not exceed the maximum aerobic level.

Figure 4:
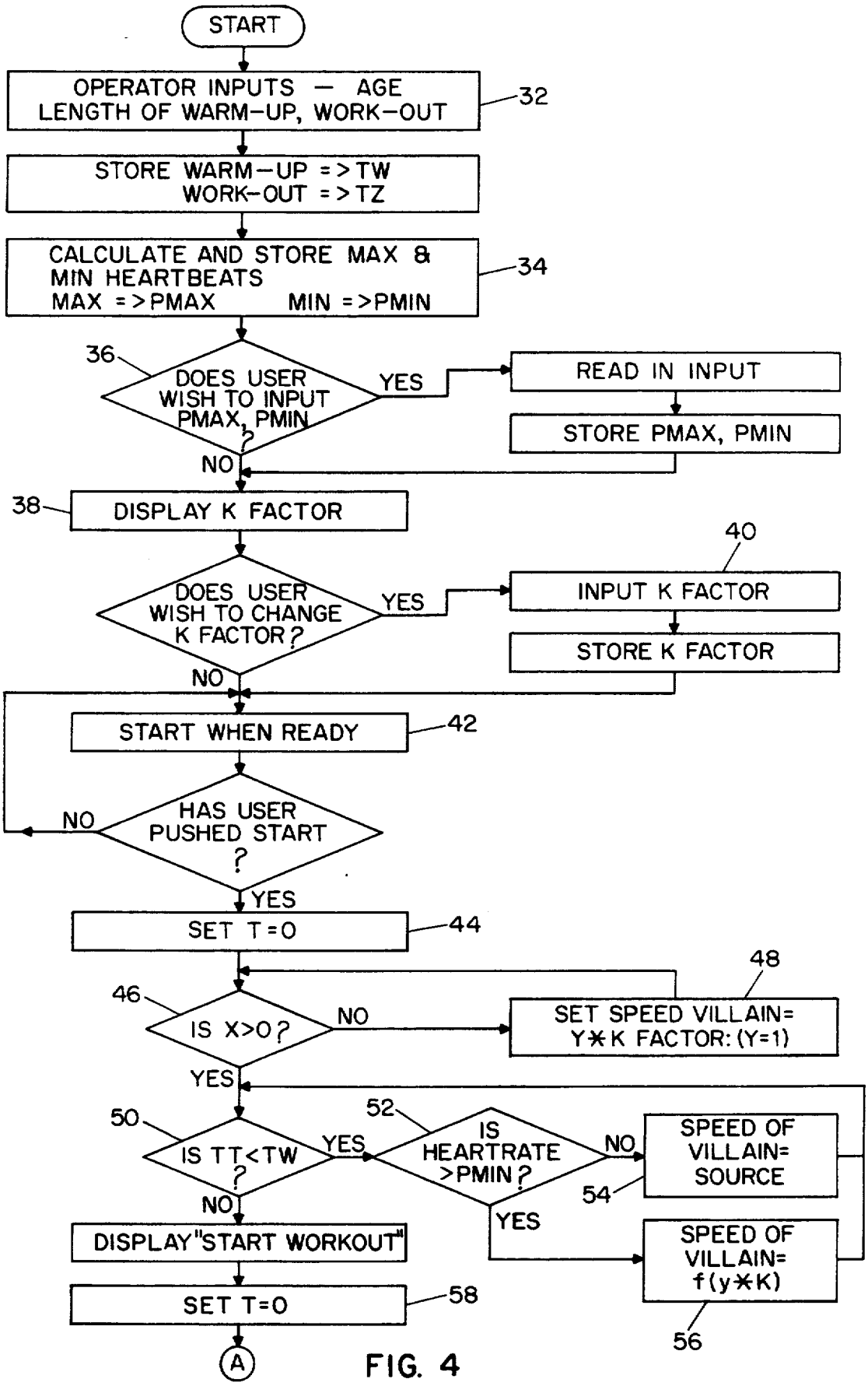
FIG. 4 is a flowchart of the logic of a video game arranged according to the invention that accepts input from the speed sensor and heart monitor.
Figure 4:
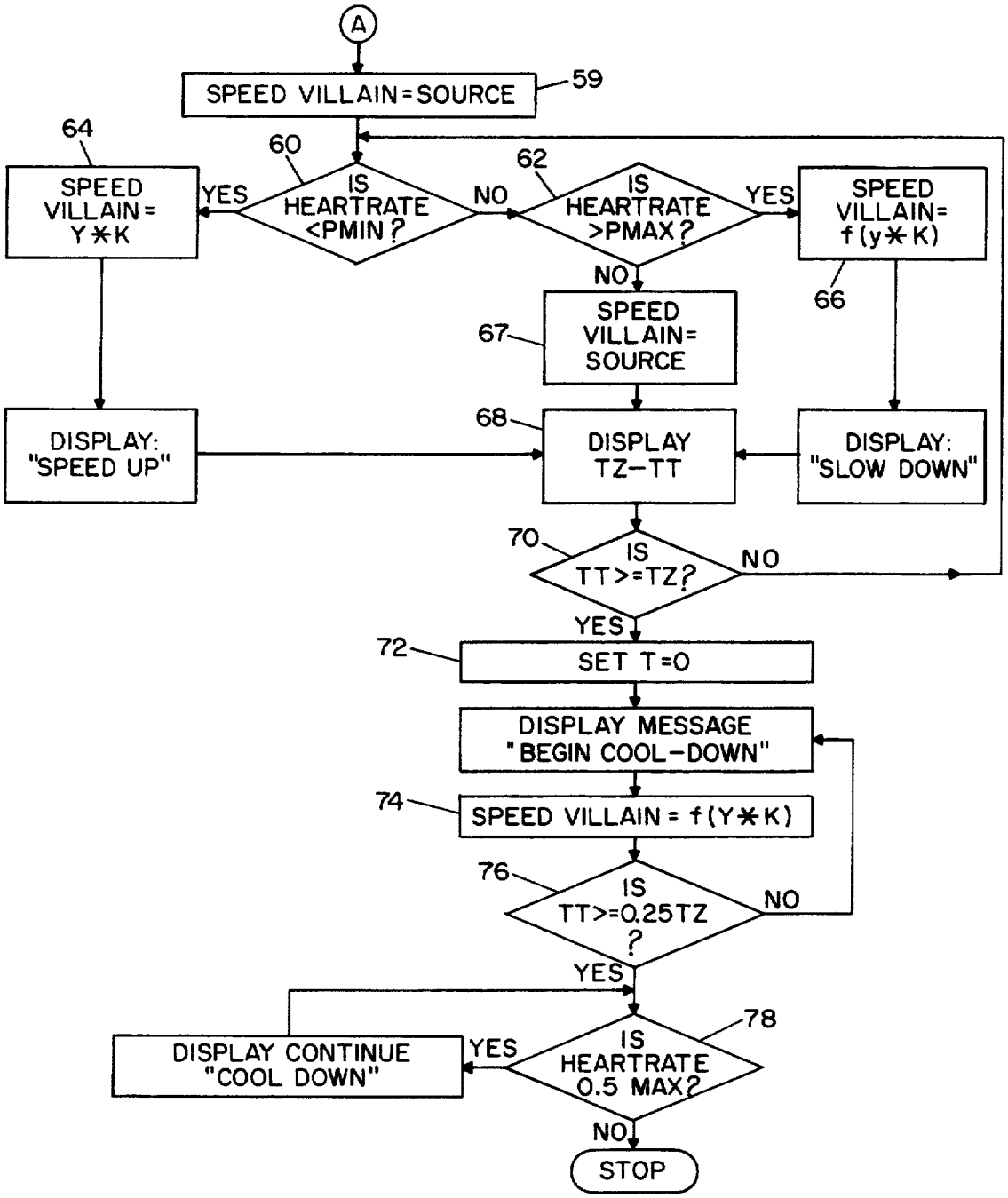

FIG. 4 describes the flow-chart for the logic of the video game in accordance with a program stored in read only memory 18. Prior to starting a work-out, the exerciser inputs his age, length of warm-up (Tw) and length of main work-out (Tz) at step 30. According to the recommended level of exercise described in FIGS. 2 and 3 and discussed earlier, the optimal range of heart rate required during exercise for a person of the entered age is calculated and displayed in step 34. Should the exerciser wish to override the recommended heart rate, perhaps on the advice of his doctor, a different upper (Pmax) and lower (Pmin) heart rate may be manually entered at step 36.

The purpose of recording the heart rate is to ensure that the exerciser exercises optimally, but does not over exert his or her heart. Should the heart rate of the exerciser fall outside the optimal heart rate range calculated, or the manually entered range, the speed of the opposition or villain changes in relation to the speed of the source. The variable that controls the villain's relative speed, and thus represents the advantage or disadvantage the villain will have in relation to the source, is a settable constant called the K factor. The video game will have a default K factor value, between 1.1 and 1.5 for example, and it is displayed after the exerciser has inputted his workout information at step 38. Should the exerciser wish to change the default K factor, a new K factor may be manually entered at step 40.

With the required information entered, the exercise routine can commence once the operator presses the start button at step 42, whereupon the internal timer (T) begins at step 44, and the time remaining in the warm-up is displayed on the screen.

Since the speed the source or one player moves in the video game is proportional to the speed that the exerciser uses the exercise machine, if the exerciser fails to begin the workout, the source or one player will remain stationary on the screen at step 46. The villain immediately gets an advantage versus the source, which at this point is stationary, in that its speed is the game's preset speed (set at 1) multiplied by the K factor effect at step 48. For example, if the K factor has been set to 1.5, the villain's speed will be one and a half times faster than its preset value. The villain will gain rapidly on the source, prompting the exerciser to begin his warm-up, and get away from the villain.

While the warm-up continues in step 50, the heart rate of the exerciser is continually checked to ensure that it does not deviate from the optimal work-out rate at step 52. As long as the exerciser's heart rate remains below the minimum aerobic rate Pmin the villain's speed is directly proportional to the source's speed Y (see step 54). However should the heart rate exceed the minimum aerobic rate, thus indicating that the exerciser is working-out too vigorously during the warm-up, the villain's speed is reduced below that of the source (See step 56) by factor which is the product of f and K. For example if $K=1.5$ and $f=0.6$; then the villain's speed is 0.9 times that of the source. This will prompt the exerciser to slow down.

Once the warm-up period ceases as detected in step 50, the timer (T) resets in step 58, and the work-out commences. The villain's speed is reset to the speed of the source in step 59. The heart rate is continually monitored during the work-out in step 60. If the heart rate falls below the minimum aerobic rate Pmin, the villain's speed increases in relation to the source by the K factor in step 64. A message on the screen then advises the exerciser to increase his level of activity. Conversely, should it be detected in step 62 that the heart rate exceeds the optimal aerobic rate Pmax, the speed of the villain decreases in relation to that of the source in step 66 (in a manner similar to that described above in step 56) and a message cautions the exerciser to slow down. If however, exercise is occurring within the optimal range, then the speed of the villain equals the speed of the source in step 67. The time remaining in the work-out is recalculated and refreshed on the display in step 68 and a check is made in step 70 on whether the total time Tt elapsed in the main work-out period has reached the time Tz which has been preset. If not the program returns to step 60. Once the main work-out ceases as detected in step 70, the timer (T) is reset in step 72, and the source gains a continual speed advantage versus the villain in step 74, prompting the exerciser to slow down.

The cool-down period continues for at least a quarter of the time of the work-out 76. If the heart rate at the end of this period still exceeds 50% of the maximal attainable heart rate 78, a message is displayed recommending the exerciser to continue the cool-down period. The cool-down period thus continues until the heart rate of the exerciser drops to below 50% of the maximal attainable heart rate.

Although a preferred embodiment of the invention has been shown and described, numerous variations and modifications will readily occur to those skilled in the art. For example, the villain in the video game may be programmed to go faster, rather than slower relative to the player or source when the heart rate exceeds the maximum aerobic level. The exerciser in this circumstance will get immediate feedback that exceeding the maximum aerobic limit will not place him in any greater advantage relative to the villain (and will actually be placed in a disadvantage relative to the villain) when the maximum aerobic limit is exceeded. This is consistent with research on exercise indicating that exercise levels exceeding the maximum aerobic limit provide little additional aerobic benefit over exercise within the preferred aerobic range, and may actually pose some risks for persons not in excellent physical condition. The present invention is not limited to the specific embodiment disclosed and the scope of the invention is limited only by the appended claims.

What is claimed is:

1. A combination exercise device and game apparatus, comprising:

an exercise device for aerobic activity;

means for sensing the activity output level of said aerobic exercise device, and for outputting an activity level signal having a characteristic indicative of said activity level;

means for sensing the heart rate of the user;

a video game having at least one user operated control for controlling the actions of at least one player, regulating means for regulating the relative action of said one player and one of an opposition piece or obstacle, display means for displaying the one player and the one of said opposition piece or obstacle, said regulating means further including means for increasing the speed of both the one player and the one of the opposition piece or obstacle in response to and in proportion to the activity level, and the regulating means further including means for rendering the video game more difficult for the one player relative to the opposition piece or obstacle by increasing the speed of the opposition piece or obstacle in response to the heart rate of the user falling below a first predetermined level.

2. The apparatus according to claim 1, wherein the exercise device is a bicycle.

3. The apparatus according to claim 1, wherein the exercise device is a treadmill.

4. The apparatus according to claim 1, wherein the exercise device is a stair climbing device.

5. The apparatus according to claim 1 wherein said first predetermined level corresponds to a minimum aerobic activity level for the user.

6. The apparatus according to claim 1 wherein the display means comprises means for displaying the heart rate of the user.

7. The apparatus according to claim 1 wherein the display means comprises means for displaying the output level of the exercise device.

8. The apparatus according to claim 1, wherein the regulating means renders the video game less difficult to the one player in response to the activity level exceeding a second predetermined level, said second predetermined level being greater than said first predetermined level.

9. The apparatus according to claim 1, wherein the first predetermined level is selected according to the user's age.

10. The apparatus according to claim 8, wherein the first predetermined level corresponds to the minimum heart rate of the user in an optimum aerobic exercise range, and wherein the second predetermined level corresponds to the maximum heart rate of the user in an optimum aerobic exercise range.

11. A game apparatus useable with an exercise device, comprising:

means for sensing the activity output level of an aerobic exercise device, and for outputting an activity level signal having a characteristic indicative of said activity level;

means for sensing the heart rate of a user of the aerobic exercise device;

a video game having at least one user operated control for controlling the actions of at least one player, regulating means for regulating the relative actions of one of said one player and an opposition piece or obstacle, display means for displaying the one player and the one of said opposition piece or obstacle, said regulating means further including means for increasing the speed of both the one player and the one of the opposition piece of obstacle in response to and in proportion to the activity level, the regulating means further including means for rendering the video game more difficult for the one player relative to the opposition piece or obstacle by increasing the speed of the opposition piece or obstacle in response to the heart rate of the user falling below a first predetermined level.

12. The apparatus according to claim 11, further including an exercise device.

13. The apparatus according to claim 12, wherein the exercise device is an exercise bicycle.

14. The apparatus according to claim 12, wherein the exercise device is a treadmill.

15. The apparatus according to claim 12, wherein the exercise device is a stair climbing device.

16. The apparatus according to claim 11, wherein said first predetermined level corresponds to the minimum aerobic activity level for the user.

17. The apparatus according to claim 11, wherein the display means comprises means for displaying the heart rate of the user.

18. The apparatus to claim 11, wherein the display means comprises means for displaying the output level of the exercise device.

19. The apparatus according to claim 11, wherein the regulating means renders the video game less difficult to the one player in response to the activity level exceeding a second predetermined level, said second predetermined level being greater than said first predetermined level.

20. The apparatus according to claim 11, wherein the first predetermined level is selected according to the user's age.

21. The apparatus according to claim 19, wherein the first predetermined level corresponds to the minimum heart rate of the user in an optimum aerobic exercise range, and wherein the second predetermined level corresponds to the maximum heart rate of the user in an optimum aerobic exercise range.

22. An exercise motivation apparatus useable with an aerobic exercise device and a video game having at least one user operated control for controlling the actions of said one player and at least one player, and which controls the relative actions of one of an opposition piece or obstacle, and which displays the one player and the one of said opposition piece or obstacle, comprising:

means for sensing the activity output level of an aerobic exercise device, and for outputting an activity level signal having a characteristic indicative of said activity level;

means for sensing the heart rate of a user of the aerobic exercise device; and regulating means for increasing the speed of both the one player and the one of the opposition piece or obstacle by increasing the speed of the opposition piece or obstacle in response to and in proportion to the activity level, the regulating means further including means for rendering the video game more difficult for the one player relative to the opposition piece or obstacle in response to the heart rate of the user falling below a first predetermined level.

23. The apparatus according to claim 22, further including an exercise device.

24. The apparatus according to claim 23, wherein the exercise device is an exercise bicycle.

25. The apparatus according to claim 23, wherein the exercise device is a treadmill.

26. The apparatus according to claim 23, wherein the exercise device is a stair climbing device.

27. The apparatus according to claim 22, wherein said first predetermined level corresponds to the minimum aerobic activity level for the user.

28. The apparatus according to claim 22, further including display means for displaying the heart rate of the user.

29. The apparatus according to claim 22, further including display means for displaying the output level of the exercise device.

30. The apparatus according to claim 22, wherein the regulating means renders the video game less difficult to the one player in response to the activity level exceeding a second predetermined level, said second predetermined level being greater than said first predetermined level.

31. The apparatus according to claim 22, wherein the first predetermined level is selected according to the user's age.

32. The apparatus according to claim 30, wherein the first predetermined level corresponds to the minimum heart rate of the user in an optimum aerobic exercise range, and wherein the second predetermined level corresponds to the maximum heart rate of the user in an optimum aerobic exercise range.

33. A combination exercise device and game apparatus, comprising:

an exercise device for aerobic activity;

means for sensing the activity output level of said aerobic exercise device, and for outputting an activity level signal having a characteristic indicative of said activity level;

means for sensing the heart rate of the user;

timing means for measuring the length of time that a user has been using the exercise device, to provide at least two different exercise phases, including a first phase until a certain first time period is reached and a second phase after said first time period is reached;

a video game having at least one user operated control for controlling the actions of at least one player, regulating means for regulating the relative action of said one player and one of an opposition piece or obstacle, and display means for displaying the one player and the one of said opposition piece or obstacle;

said regulating means further including means for increasing the speed of both the one player and the one of the opposition piece or obstacle in response to and in proportion to the activity level;

said regulating means including means for rendering the game more difficult for the one player relative to the opposition piece or obstacle by increasing the speed of the opposition piece or obstacle in response to the heart rate of the user rising above a first predetermined level when the timing means indicates that the user is in the first phase; and said regulating including means for rendering the video game more difficult for the one player relative to the opposition piece or obstacle by increasing the speed of the opposition piece or obstacle in response to the heart rate of the user falling below the first predetermined level when the timing means indicates that the user is in the second phase.

*34. A combination exercise device and game apparatus, comprising:*

*a) an exercise device for aerobic activity;*

*b) means for sensing the output level of said exercise device, and for outputting an output level signal having a characteristic indicative of said output level;*

*c) means for sensing the heart rate of a user, and for outputting a heart rate signal having a characteristic indicative of said heart rate;*

*d) a video game including display means for displaying said video game; and*

*e) regulating means including:*

*i 1) means for adjusting the difficulty of the play of said video game according to said heart rate signal; and*

*2) means for adjusting the difficulty of the play of said video game according to said output level signal.*

*35. The apparatus of claim 34, further comprising at least one user-operated control for controlling the play of said video game.*

*36. The apparatus of claim 35, wherein said apparatus includes a first user-operated control for controlling a first aspect of the play of said video game with one of said user's hands and a second user-operated control for controlling a second aspect of the play of said video game with the other of said user's hands.*

*37. The apparatus of claim 34, wherein:*

*said video game has a plurality of levels of difficulty of play;*

*said regulating means increases the level of difficulty of play in response to said heart rate signal falling below a first predetermined level; and*

*said regulating means decreases the level of difficulty of play as said output level signal increases and increases the level of difficulty of play as said output level signal decreases.*

*38. The apparatus of claim 37, wherein said first predetermined level corresponds to the minimum heart rate of said user in an optimum aerobic exercise range.*

*39. The apparatus of claim 37, wherein:*

*said video game comprises a source and at least one opposition;*

*said regulating means increases the speed of said opposition relative to said source in response to said heart rate signal falling below said first predetermined level; and*

*said regulating means increases the speed of said opposition relative to said source as said output level signal decreases and decreases the speed of said opposition relative to said source as said output level signal increases.*

*40. The apparatus of claim 37, wherein said regulating means decreases the level of difficulty of play in response to said heart rate signal exceeding a second predetermined level, said second predetermined level being greater than said first predetermined level.*

*41. The apparatus of claim 34, wherein said regulating means adjusts the play of said video game according to a specified exercise profile having at least two exercise phases.*

*42. The apparatus of claim 41, wherein said video game comprises a source and at least one opposition, and said regulating means adjusts the speed of said opposition relative to said source according to said specified exercise profile.*

*43. The apparatus of claim 34, wherein said exercise device is one of an exercise bicycle, a treadmill, and a stair climbing device.*

*44. The apparatus of claim 34, wherein said display means displays information indicative of said heart rate of said user and said output level of said exercise device.*

*45. A game apparatus useable with an exercise device, comprising:*

*a) means for sensing the output level of said exercise device, and for outputting an output level signal having a characteristic indicative of said output level;*

*b) means for sensing the heart rate of a user, and for outputting a heart rate signal having a characteristic indicative of said heart rate;*

*c) a video game including display means for displaying said video game; and*

*d) regulating means including:*

*1) means for adjusting the difficulty of the play of said video game according to said heart rate signal; and*

*2) means for adjusting the difficulty of the play of said video game according to said output level signal.*

*46. The apparatus of claim 45, further comprising at least one user-operated control for controlling the play of said video game.*

*47. The apparatus of claim 46, wherein said apparatus includes a first user-operated control for controlling a first aspect of the play of said video game with one of said user's hands and a second user-operated control for controlling a second aspect of the play of said video game with the other of said user's hands.*

*48. The apparatus of claim 45, wherein:*

*said video game has a plurality of levels of difficulty of play;*

*said regulating means increases the level of difficulty of play in response to said heart rate signal falling below a first predetermined level; and*

*said regulating means decreases the level of difficulty of play as said output level signal increases and increases the level of difficulty of play as said output level signal decreases.*

*49. The apparatus of claim 48, wherein said first predetermined level corresponds to the minimum heart rate of said user in an optimum aerobic exercise range.*

*50. The apparatus of claim 48, wherein:*

*said video game comprises a source and at least one opposition;*

*said regulating means increases the speed of said opposition relative to said source in response to said heart rate signal falling below said first predetermined level; and*

*said regulating means increases the speed of said opposition relative to said source as said output level signal decreases and decreases the speed of said opposition relative to said output level signal increases.*

*51. The apparatus of claim 48, wherein said regulating means decreases the level of difficulty of play in response to said heart rate signal exceeding s second predetermined level, said second predetermined level being greater than said first predetermined level.*

*52. The apparatus of claim 45, wherein said regulating means adjusts the play of said video game according to a specified exercise profile having at least two exercise phases.*

*53. The apparatus of claim 52, wherein said video game comprises a source and at least one opposition, and said regulating means adjusts the speed of said opposition relative to said source according to said specified exercise profile.*

*54. The apparatus of claim 45, wherein said exercise device is one of an exercise bicycle, a treadmill, and a stair climbing device.*

*55. The apparatus of claim 45, wherein said display means displays information indicative of said heart rate of said user and said output level of said exercise device.*

*56. An exercise motivation apparatus useable with an exercise device and a video game including display means for displaying said video game, comprising:*

*a) means for sensing the output level of said exercise device, and for outputting an output level signal having a characteristic indicative of said output level;*

*b) means for sensing the heart rate of a user, and for outputting a heart rate signal having a characteristic indicative of said heart rate; and*

*c) regulating means including:*

*1) means for adjusting the difficulty of the play of said video game according to said heart rate signal; and*

*2) means for adjusting the difficulty of the play of said video game according to said output level signal.*

*57. The apparatus of claim 56, further comprising at least one user-operated control for controlling the play of said video game.*

*58. The apparatus of claim 57, wherein said apparatus includes a first user-operated control for controlling a first aspect of the play of said video game with one of said user's hands and a second user-operated control for controlling a second aspect of the play of said video game with the other of said user's hands.*

*59. The apparatus of claim 56, wherein:*

*said video game has a plurality of levels of difficulty of play;*

*said regulating means increases the level of difficulty of play in response to said heart rate signal falling below a first predetermined level; and* said regulating means decreases the level of difficulty of play as said output level signal increases and increases the level of difficulty of play as said output level signal decreases.

*60. The apparatus of claim 59, wherein said first predetermined level corresponds to the minimum heart rate of said user in an optimum aerobic exercise range.*

*61. The apparatus of claim 59, wherein:*

*said video game comprises a source and at least one opposition;*

*said regulating means increases the speed of said opposition relative to said source in response to said heart rate signal falling below said first predetermined level; and*

*said regulating means increases the speed of said opposition relative to said source as said output level signal decreases and decreases the speed of said opposition relative to said source as said output level signal increases.*

*62. The apparatus of claim 59, wherein said regulating means decreases the level of difficulty of play in response to said heart rate signal exceeding a second predetermined level, said second predetermined level being greater than said first predetermined level.*

*63. The apparatus of claim 56, wherein said regulating means adjusts the play of said video game according to a specified exercise profile having at least two exercise phases.*

*64. The apparatus of claim 63, wherein said video game comprises a source and at least one opposition, and said regulating means adjusts the speed of said opposition relative to said source according to said specified exercise profile.*

*65. The apparatus of claim 56, wherein said exercise device is one of an exercise bicycle, a treadmill, and a stair climbing device.*

*66. The apparatus of claim 56, wherein said display means displays information indicative of said heart rate of said user and said output level of said exercise device.*

*67. A combination exercise device and game apparatus, comprising:*

*a) an exercise device for aerobic activity;*

*b) means for sensing the output level of said exercise device, and for outputting an output level signal having a characteristic indicative of said output level;*

*c) means for sensing the heart rate of a user, and for outputting a heart rate signal having a characteristic indicative of said heart rate;*

*d) a video game including:*

*1) display means for displaying said video game;*

*2) a plurality of levels of difficulty of play; and*

*3) at least one user-operated control for controlling the play of said video game;*

*e) regulating means including:*

*1) means for adjusting the level of difficulty of said video game according to said heart rate signal, wherein said level of difficulty is increased in response to said heart rate signal falling below a first predetermined level;*

*2) means for adjusting the level of difficulty of said video game according to said output level signal, wherein said level of difficulty increases as said output level signal decreases and said level of difficulty decreases as said output level signal increases; and*

*3) means for adjusting the level of difficulty of said video game according to a specified exercise profile having at least two exercise phases.*

* * * * *